United States Patent
Nelson et al.

(10) Patent No.: US 7,482,493 B2
(45) Date of Patent: *Jan. 27, 2009

(54) METHOD FOR THE PRODUCTION OF PHENOL AND ACETONE

(75) Inventors: Mark Nelson, Mount Vernon, IN (US); Willem Lodewyk Sederel, Kalmhout (BE); Arkady Samuilovich Dyckman, Saint Petersburg (RU); Ilya Nikolaevich Grebenshchikov, Saint Petersburg (RU); Viktor Vladimirovich Pinson, Saint Petersburg (RU); Andrey Vladimirovich Zinenkov, Saint Petersburg (RU)

(73) Assignee: SABIC Innovative Plastics IP B.V., Bergen op Zoom (NL)

( * ) Notice: Subject to any disclaimer, the term of this patent is extended or adjusted under 35 U.S.C. 154(b) by 0 days.

This patent is subject to a terminal disclaimer.

(21) Appl. No.: 11/861,374

(22) Filed: Sep. 26, 2007

(65) Prior Publication Data

US 2008/0214872 A1 Sep. 4, 2008

(30) Foreign Application Priority Data

Mar. 1, 2007 (RU) .............................. 2007108707

(51) Int. Cl.
*C07C 45/00* (2006.01)
*C07C 37/08* (2006.01)

(52) U.S. Cl. .................. 568/385; 568/768; 568/798

(58) Field of Classification Search ................ 568/385, 568/798

See application file for complete search history.

(56) References Cited

U.S. PATENT DOCUMENTS

| | | | | |
|---|---|---|---|---|
| 3,271,457 | A * | 9/1966 | Bewley et al. | 568/385 |
| 4,246,203 | A * | 1/1981 | Wirth | 568/385 |
| 6,057,483 | A | 5/2000 | Zakoshansky et al. | |
| 7,109,385 | B2 * | 9/2006 | Tatake et al. | 568/798 |
| 2005/0222466 | A1 | 10/2005 | Tatake et al. | |

FOREIGN PATENT DOCUMENTS

| | | |
|---|---|---|
| RU | 2068404 C1 | 10/1996 |
| RU | 2121477 C1 | 11/1998 |
| RU | 2291852 C1 | 1/2007 |

OTHER PUBLICATIONS

PCT International Search Report for International Application No. PCT/US2008/055808.
PCT International Search Report for International Application No. PCT/US2008/055810.
Zakoshansky, V.M. Scientific Publication, Conference Materials, Development Prospects for Chemical Processing of Fossil Fuel. "Cumene Process of Phenol-Acetone Production—History and Evolution". Khimizdata, St. Petersburg, RU pp. 25-39.
Zakoshansky, V.M. "Direction For the Development of Phenolic Process—Safety, Selectivity and Quality of the Products: I. Cumene Oxidation into Cumene Hydroperioxide (CHP)". ISBN 5-901065-94-8. Process of Oil Refining and Petrochemistry. SP6., 2005. pp. 89-107.
Zakoshansky, V.M. "Direction For Phenol Process Development—Security, Selectivity Quality and Marketable Product: II. Decomposition of Technical Cumyl Hydroperioxide". ISBN 5-901065-94-8. Process of Oil Refining and Petrochemistry. SP6., 2005. pp. 108-130.
Vasileva, I.I. and Zakoshansky, V.M. "Direction of Development Phenolic Process—Safety, Selectivity and Quality of the Commodity Products: III. Technologies of Separation and Quality of Products". ISBN 5-901065-94-8. Process of Oil Refining and Petrochemistry. SP6., 2005. pp. 131-154.
Kirk-Othmer Encyclopedia of Chemical Technology. Fourth Edition, vol. 18, Phenol. pp. 592-602.

* cited by examiner

*Primary Examiner*—Sikarl A Witherspoon

(57) ABSTRACT

A method for the production of phenol and acetone from a cumene hydroperoxide mixture comprises: decomposing the cumene hydroperoxide mixture in the presence of a catalyst mixture to form a mixture comprising phenol and acetone, wherein the method further comprises: a) forming the catalyst mixture in a catalyst formation reactor by combining sulfuric acid and phenol in a weight ratio of from 2:1 to 1:1000; b) holding the catalyst mixture in the catalyst formation reactor at a temperature of about 20 to 80° C. for about 1 to 600 minutes; and c) adding the catalyst mixture to the cumene hydroperoxide mixture to form the phenol and acetone mixture. Running the process in this manner reduces the yield of hydroxyacetone and, consequently, improves the quality of the commercial phenol. Moreover, this method reduces consumption of sulfuric acid in comparison with the process in which sulfuric acid is used as catalyst.

16 Claims, No Drawings

METHOD FOR THE PRODUCTION OF PHENOL AND ACETONE

CROSS REFERENCE TO RELATED APPLICATIONS

This application is related to the patent application entitled "METHOD FOR THE PRODUCTION OF PHENOL AND ACETONE," concurrently filed (which claims priority from Russian Application Serial No. 2007108708). This disclosure is hereby fully incorporated herein by reference.

BACKGROUND

The present invention relates to industrial organic synthesis, specifically to production of phenol and acetone by the cumene method.

A well-known method for the production of phenol and acetone by oxidation of cumene with atmospheric oxygen, followed by the acid-catalytic decomposition of cumene hydroperoxide permits both end products to be produced with high yield (see, for example, Kruzhalov B. D., Golovanenko B. N., *Combined Production of Phenol and Acetone*, Moscow, Goskhimizdat, 1964, or Kirk-Othmer Encyclopedia of Industrial Chemistry). This method is widely used to produce these products and is the principal technique used in world practice.

Methods are known for producing phenol and acetone in which, to reduce the yield of phenol tar, cumene oxidation products containing cumene hydroperoxide (CHP), cumene, and dimethylphenylcarbinol (DMPC) cleavage in the presence of sulfuric acid to be separated in two stages. In the first stage, at a temperature of 55 to 80° C., most of the CHP (97 to 99%) is decomposed and dicumyl peroxide (DCP) is synthesized from DMPC and CHP. In the second stage, acetone is added and the process fulfilled at a temperature of 80 to 146° C. to the obtained reaction mixture containing phenol, acetone, and alpha-methylstyrene, decomposing DCP and the remaining CHP and DMPC. The addition is made in an amount of 1.5 to 1.8 times the original concentration of acetone. Water is also added. In some cases the acid is partially neutralized with ammonia before the second separation stage in order to ensure optimal acidity of the catalyst. Breakdown of DCP formed in the first stage, decomposition of the remaining CHP and dehydration of the remaining DMPC occur here (See, for example, Russian Patent Nos. 2068404, 2121477, 2142932).

These methods significantly reduce the amount of formed byproducts in comparison with decomposition in one stage, whereas the amount of formed byproduct (hydroxyacetone) remains at a high level (and sometimes increases).

Hydroxyacetone is a source of formation of 2-methylbenzofuran, which is difficult to separate from phenol and which causes deterioration in the color indices of the commercial phenol. Elimination of hydroxyacetone from phenol by alkaline treatment complicates the process (Vasil'eva I. I., Zakoshanski V. M., *Petroleum Processing and Petrochemistry*, St. Petersburg, "Giord", 2005, page 344).

The use of a two-stage method to decompose CHP improves the process indices for the synthesis of phenol and acetone, but is associated with the use of a large amount of equipment in comparison with a one-stage CHP decomposition process, and is technically more complicated. For this reason, a large number of installations that use CHP decomposition in one stage continue to be operated. For example, according to U.S. Pat. No. 4,246,203, CHP decomposition is carried out in one stage at a temperature from 120 to 200° C., and almost all of the reaction mass is evaporated using the heat of the decomposition reaction. The best catalyst is sulfuric acid, which is fed to the CHP decomposition reactor in the form of a solution in acetone, acetophenone, cumene or their mixtures, with a concentration from 0.005 to 0.2% (50 to 2000 parts per million (ppm)). The acid concentration in the reaction mass is not mentioned, but it should be higher since the acid remains in the non-volatile residue after evaporation of the reaction products of CHP decomposition.

The method closest to the proposed method for the production of phenol and acetone by acid-catalyzed decomposition of cumene hydroperoxide (CHP), and the simplest technology, is the method described in U.S. Pat. No. 3,271,457. According to the patent, CHP decomposition to phenol and acetone occurs in a reactor to which CHP and catalyst (acid) are fed in an amount at which the acid concentration in the reaction mass is from 0.05 to 10%, preferably from 0.1 to 2%. A mixing/distributing device is installed in the vapor phase above the surface of the reaction mass in which the CHP-containing feedstock is mixed with acetone that is evaporated from the heat of reaction of CHP decomposition on entering the reactor, then condensed in a condenser, and sent back to dilute the feedstock. Thus, the heat released during the reaction is removed and CHP is diluted, which increases the process safety. The process of CHP decomposition is run at a temperature from 50 to 90° C., preferably 70 to 85° C. With this process scheme, there is a significant acetone excess in the CHP decomposition zone in comparison with the stoichiometric ratio of phenol/acetone, and also a very high concentration of acid. The result of this approach is a high yield of hydroxyacetone, the presence of which causes a deterioration in the quality of the commercial phenol.

SUMMARY OF THE INVENTION

In an embodiment, a method for the production of phenol and acetone from a cumene hydroperoxide mixture comprises: decomposing the cumene hydroperoxide mixture in the presence of a catalyst mixture to form a mixture comprising phenol and acetone, wherein the method further comprises: a) forming the catalyst mixture in a catalyst formation reactor by combining sulfuric acid and phenol in a weight ratio of from 2:1 to 1:1000; b) holding the catalyst mixture in the catalyst formation reactor at a temperature of about 20 to 80° C. for about 1 to 600 minutes; and c) adding the catalyst mixture to the cumene hydroperoxide mixture to form the phenol and acetone mixture.

DETAILED DESCRIPTION OF THE INVENTION

In order to reduce the yield of hydroxyacetone (HA) during decomposition of CHP, it has been proposed to decompose technical CHP in a medium of reaction products in the presence of a catalyst prepared by mixing phenol with sulfuric acid directly before introduction to the CHP decomposition reactor. For this purpose, molten phenol is mixed with sulfuric acid in a concentration of at least 75%, in a weight ratio of 1:2 to 1000:1, respectively, and the obtained mixture is held in a separate reactor at a temperature from 20 to 80° C. for 1 to 600 minutes, whereupon the catalyst is fed to the CHP decomposition reactor. In some embodiments, the sulfuric acid is fuming sulfuric acid (oleum). The catalyst prepared and obtained in this way is more active in comparison with the same amount of sulfuric acid from which it was prepared.

In an embodiment, a method for the production of phenol and acetone from a cumene hydroperoxide mixture comprises: decomposing the cumene hydroperoxide mixture in the presence of a catalyst mixture to form a mixture comprising phenol and acetone, wherein the method further comprises: a) forming the catalyst mixture in a catalyst formation reactor by combining sulfuric acid and phenol in a weight ratio of from 2:1 to 1:1000; b) holding the catalyst mixture in the catalyst formation reactor at a temperature of about 20 to 80° C. for about 1 to 600 minutes; and c) adding the catalyst mixture to the cumene hydroperoxide mixture to form the phenol and acetone mixture. In an embodiment, the sulfuric acid is an aqueous sulfuric acid solution comprising at least 75 wt. % sulfuric acid, and in another embodiment, the sulfuric acid is fuming sulfuric acid (oleum). In an embodiment, the reaction temperature for decomposing the cumene hydroperoxide is from about 60 to 80° C.

In an embodiment, the phenol and acetone mixture formed has a reduced level of hydroxyacetone as compared to a phenol and acetone mixture formed using a catalyst that is only sulfuric acid. In another embodiment, the catalyst mixture in step b) is held at a temperature of from about 35 to 45° C. In another embodiment, the reaction time in step b) is from about 60 to about 300 minutes.

In another embodiment, a method for the production of phenol and acetone from a cumene hydroperoxide mixture comprises: decomposing the cumene hydroperoxide mixture in the presence of a catalyst mixture to form a mixture comprising phenol and acetone, wherein the method further comprises: a) forming the catalyst mixture in a catalyst formation reactor by combining sulfuric acid and phenol in a weight ratio of from 2:1 to 1:1000, wherein the sulfuric acid is an aqueous sulfuric acid solution comprising at least 75 wt. % sulfuric acid; b) holding the catalyst mixture in the catalyst formation reactor at a temperature of about 20 to 80° C. for about 1 to 600 minutes; and c) adding the catalyst mixture to the cumene hydroperoxide mixture to form the phenol and acetone mixture.

In another embodiment, a method for the production of phenol and acetone from a cumene hydroperoxide mixture comprises: decomposing the cumene hydroperoxide mixture in the presence of a catalyst mixture to form a mixture comprising phenol and acetone, wherein the method further comprises: a) forming the catalyst mixture in a catalyst formation reactor by combining sulfuric acid and phenol in a weight ratio of from 2:1 to 1:1000, wherein the sulfuric acid is an aqueous sulfuric acid solution comprising at least 75 wt. % sulfuric acid; b) holding the catalyst mixture in the catalyst formation reactor at a temperature of about 35 to 45° C. for about 60 to 300 minutes; and c) adding the catalyst mixture to the cumene hydroperoxide mixture to form the phenol and acetone mixture, wherein the phenol and acetone mixture formed has a reduced level of hydroxyacetone as compared to a phenol and acetone mixture formed using a catalyst that is only sulfuric acid.

The process of CHP decomposition is run in one stage. The heat released during decomposition of CHP is either taken off with a heat exchanger or by evaporation of the acetone added to the reaction mass. The acetone is condensed and returned to the CHP decomposition reactor. The process is run at a temperature of 60 to 80° C.

Under these process conditions, the use of technical CHP having a similar composition reduces the hydroxyacetone concentration in the reaction mass emerging from the CHP decomposition reactor from a starting range of from 0.12 to 0.2% to a final range of from 0.07 to 0.12 wt. %, which significantly affects the quality of the commercial phenol. Moreover, the reduction in the amount of employed sulfuric acid leads to a reduction in the consumption of alkali used to neutralize the acid, which ultimately reduces the amount of mineral wastes, such as sodium sulfate, of the production process.

The invention is illustrated by the following non-limiting examples.

EXAMPLES

Example 1

Decomposition of cumene hydroperoxide was carried out on a pilot unit in the form of a reactor with a volume of 12 mL, equipped with a circulation loop to mix the reaction mass and a water jacket to maintain the assigned temperature. To prepare the catalyst, a reactor with a volume of 10 μL was used, and sulfuric acid and phenol were fed by pumps to the reactor. Catalyst and feedstock were fed to the stream of reaction mass at the input to the reactor. The composition of the feedstock is shown in Table 1.

TABLE 1

Feedstock used for decomposition of CHP

| | Component | Content, wt. % |
|---|---|---|
| 1 | Cumene hydroperoxide (CHP) | 81.73 |
| 2 | Cumene | 10.9 |
| 3 | Dimethylphenylcarbinol (DMPC) | 5.48 |
| 4 | Acetophenone | 1.0 |
| 5 | Water | 0.3 |
| 6 | Dicumyl peroxide (DCP) | 0.35 |
| 7 | Unidentified | 0.49 |

Sulfuric acid was also fed to the catalyst synthesis reactor at a rate of 3 μL/h, phenol was fed at a rate of 6 μL/h, which corresponds to a concentration in the reaction medium of 0.02 wt. %, and the holding time in the reactor was 70 minutes at a temperature of 45° C. The rate at which the feedstock was fed to the CHP decomposition reactor was 27 mL/h. The rate of circulation of the reaction mass was 500 mL/h. The temperature in the reactor was maintained at 75° C. by supplying a heat transfer agent of the corresponding temperature to the jacket of the reactor.

The stream emerging from the CHP decomposition reactor was cooled to room temperature and analyzed by GC. The composition of the reaction mass of CHP decomposition is shown in Table 2.

TABLE 2

Composition of reaction mass of CHP decomposition

| Component | Concentration, wt. % |
|---|---|
| Phenol | 48.82 |
| Acetone | 30.42 |
| Dicumyl peroxide (DCP) | 0.63 |
| Dimethylphenylcarbinol (DMPC) | 0.46 |
| Cumyl phenols | 1.06 |
| Sum of α-methylstyrene dimers | 0.74 |
| Acetophenone | 1.16 |
| α-Methylstyrene (AMS) | 2.00 |
| Cumene | 10.03 |
| Hydroxyacetone (HA) | 0.07 |
| Mesityl oxide | 0.01 |
| Unidentified | 0.68 |
| Heavy components of phenolic resin | 3.02 |
| Water | 0.9 |

Example 2

CHP decomposition was carried out in the same equipment as in Example 1, but the reactor for synthesis of the catalytic system had a volume of 20 µL, and a mixture having the composition shown in Table 3 was used as feedstock.

The feedstock was fed to the reactor at a rate of 10 mL/h, concentrated (~96%) sulfuric acid was fed at a rate of 1.1 µL/h, which corresponded to a concentration of 0.02 wt. %, and phenol for mixing with sulfuric acid was fed at a rate of 0.9 µL/h, which corresponded to a sulfuric acid/phenol ratio of 2:1. The mixture of phenol and sulfuric acid was held for 600 minutes at a temperature of 20° C. The circulation rate of the reaction mixture was 200 mL/h, and the temperature in the reactor was 70° C. As used herein, concentrated sulfuric acid means "commercially available usual sulfuric acid", which generally means about 93 to 96% sulfuric acid ($H_2SO_4$).

Example 3

CHP decomposition was carried out in the same equipment and under the same conditions as in Example 2, but to prepare the catalyst, 30% oleum was fed to the reactor at a rate of 0.7 µL/h, and phenol was fed at a rate of 1200 µL/h (corresponds to a phenol/sulfuric acid ratio of 1000:1 and a sulfuric acid concentration of 0.018 wt. %). The residence time of the mixture in the reactor was 1 minute at a temperature of 80° C.

Example 4

Decomposition of CHP was carried out in the same equipment as in Example 1, but to prepare the catalyst, 75% sulfuric acid was fed to the reactor at a rate of 3 µL/h, and phenol was fed at a rate of 7 µL/h. The residence time of the mixture in the reactor was about 60 minutes at a temperature of 60° C. The temperature in the CHP decomposition reactor was kept at 85° C.

TABLE 3

Feedstock used for decomposition of CHP

| | Component | Content, wt. % |
|---|---|---|
| 1 | Cumene hydroperoxide (CHP) | 81.02 |
| 2 | Cumene | 10.79 |
| 3 | Dimethylphenylcarbinol (DMPC) | 6.1 |
| 4 | Acetophenone | 1.06 |
| 5 | Water | 0.3 |
| 6 | Dicumyl peroxide (DCP) | 0.35 |
| 7 | Phenol | 0.01 |
| 8 | Unidentified | 0.37 |

The compositions of the reaction masses obtained in Examples 2 to 4 are shown in Table 4.

TABLE 4

Composition of reaction mass of CHP decomposition

| | Concentration, wt. % | | |
|---|---|---|---|
| Component | Example 2 | Example 3 | Example 4 |
| Phenol | 48.16 | 53.62 | 48.68 |
| Acetone | 29.97 | 26.83 | 29.77 |
| Dicumyl peroxide (DCP) | 0.33 | 0.25 | 0.59 |
| Dimethylphenylcarbinol (DMPC) | 0.37 | 0.31 | 0.51 |
| Cumyl phenols | 1.67 | 1.59 | 1.19 |
| Sum of α-methylstyrene dimers | 1.09 | 0.94 | 0.99 |
| Acetophenone | 1.1 | 0.90 | 1.04 |
| α-Methylstyrene (AMS) | 2.33 | 1.98 | 2.75 |
| Cumene | 10.61 | 9.79 | 10.84 |
| Hydroxyacetone (HA) | 0.09 | 0.09 | 0.08 |
| Mesityl oxide | 0.01 | 0.01 | 0.01 |
| Unidentified | 0.63 | 0.67 | 0.49 |
| Heavy components of phenolic resin | 2.96 | 2.45 | 2.43 |
| Water | 0.68 | 0.57 | 0.63 |

Example 5 (Comparative Example)

The CHP cleavage reaction was carried out essentially the same as in Example 1, but in this case the feed of composition used was as presented in Table 5. Concentrated sulfuric acid catalyst was fed at a rate of 5 µL/h directly to the cleavage reactor. The produced reaction mixture was analyzed and the final composition is presented in Table 6.

TABLE 5

CHP cleavage feed

| | Component | Concentration, wt. % |
|---|---|---|
| 1 | Cumene hydroperoxide (CHP) | 81.85 |
| 2 | Cumene | 10.59 |
| 3 | Dimethylbenzyl alcohol (DMBA) | 5.25 |
| 4 | Acetophenone | 0.97 |
| 5 | Water | 0.3 |
| 6 | Dicumylperoxide (DCP) | 0.36 |
| 7 | Unknowns | 0.68 |

TABLE 6

CHP cleavage reaction mixture composition.

| Component | Concentration, wt. % |
|---|---|
| Phenol | 49.33 |
| Acetone | 30.76 |
| Dicumylperoxide (DCP) | 0.47 |
| Dimethylbenzyl alcohol (DMBA) | 0.41 |
| Cumylphenols | 1.10 |
| α-methylstyrene dimers | 0.87 |
| Acetophenone | 1.19 |
| α-methylstyrene (AMS) | 2.13 |
| Cumene | 10.33 |
| Hydroxyacetone (HA) | 0.12 |
| Mesityl oxide | 0.01 |
| Unknowns | 0.91 |
| Phenol tar heavy components | 1.48 |
| Water | 0.89 |

The Examples and Tables show that when the catalyst is only concentrated sulfuric acid instead of a mixture of sulfuric acid and phenol, the amount of impurities is higher, as compared to the Examples where the catalyst was a mixture of sulfuric acid and phenol. As shown in Tables 4 and 6, the level of hydroxyacetone is significantly higher in Example 5 than in Examples 1 to 4. Additionally, the level of unknowns and tar is much higher in Example 5 than in Examples 1 to 4.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from essential scope thereof. Therefore, it is intended that the invention not be limited to the particular embodiment disclosed as the best mode contemplated for carrying out this invention, but that the invention will include all embodiments falling within the scope of the appended claims. One skilled in the art would recognize that in a reaction conducted using a feedstock of a different composition than the starting composition used in the experiments, the results may differ from those given in the Examples of the present invention, but the positive effect of using this invention would be retained. For example, if a different feedstock was used that had a lower weight percent CHP as a starting material, the composition mass after the reactor may be different, but it would still improve in the same manner. The effect described in the invention (the production of phenol and acetone using the catalyst system of the invention) is not attributed to the specific or particular feed composition. The CHP cleavage feed is technology realization dependent. Concentration variations can be significant. In other words, the observed effect is not CHP synthesis technology and cleavage feed preparation technology dependent.

The invention claimed is:

1. A method for the production of phenol and acetone from a cumene hydroperoxide mixture comprising: decomposing the cumene hydroperoxide mixture in the presence of a catalyst mixture to form a mixture comprising phenol and acetone, wherein the method further comprises:
    a) forming the catalyst mixture in a catalyst formation reactor by combining sulfuric acid and phenol in a weight ratio of from 2:1 to 1:1000;
    b) holding the catalyst mixture in the catalyst formation reactor at a temperature of about 20 to 80° C. for about 1 to 600 minutes; and
    c) adding the catalyst mixture to the cumene hydroperoxide mixture to form the phenol and acetone mixture.

2. The method of claim 1, wherein the sulfuric acid is an aqueous sulfuric acid solution comprising at least 75 wt. % sulfuric acid.

3. The method of claim 1, wherein the sulfuric acid is fuming sulfuric acid.

4. The method of claim 1, wherein the reaction temperature for decomposing the cumene hydroperoxide is from about 60 to 90° C.

5. The method of claim 1, wherein the sulfuric acid to phenol ratio is from 1:1 to 1:5.

6. The method of claim 1, wherein the catalyst mixture in step b) is held at a temperature of from about 35 to 45° C.

7. The method of claim 1, wherein the reaction time in step b) is from about 60 to about 300 minutes.

8. The method of claim 1, wherein the phenol and acetone mixture formed has a reduced level of hydroxyacetone as compared to a phenol and acetone mixture formed using a catalyst that is only sulfuric acid.

9. A method for the production of phenol and acetone from a cumene hydroperoxide mixture comprising: decomposing the cumene hydroperoxide mixture in the presence of a catalyst mixture to form a mixture comprising phenol and acetone, wherein the method further comprises:
    a) forming the catalyst mixture in a catalyst formation reactor by combining sulfuric acid and phenol in a weight ratio of from 2:1 to 1:1000, wherein the sulfuric acid is an aqueous sulfuric acid solution comprising at least 75 wt. % sulfuric acid;
    b) holding the catalyst mixture in the catalyst formation reactor at a temperature of about 20 to 80° C. for about 1 to 600 minutes; and
    c) adding the catalyst mixture to the cumene hydroperoxide mixture to form the phenol and acetone mixture.

10. The method of claim 9, wherein the sulfuric acid is fuming sulfuric acid (oleum).

11. The method of claim 9, wherein the reaction temperature for decomposing the cumene hydroperoxide is from about 60 to 90° C.

12. The method of claim 9, wherein the catalyst mixture in step b) is held at a temperature of from about 35 to 45° C.

13. The method of claim 1, wherein the reaction time in step b) is from about 60 to about 300 minutes.

14. The method of claim 9, wherein the phenol and acetone mixture formed has a reduced level of hydroxyacetone as compared to a phenol and acetone mixture formed using a catalyst that is only sulfuric acid.

15. A method for the production of phenol and acetone from a cumene hydroperoxide mixture comprising: decomposing the cumene hydroperoxide mixture in the presence of a catalyst mixture to form a mixture comprising phenol and acetone, wherein the method further comprises:
    a) forming the catalyst mixture in a catalyst formation reactor by combining sulfuric acid and phenol in a weight ratio of from 2:1 to 1:1000, wherein the sulfuric acid is an aqueous sulfuric acid solution comprising at least 75 wt. % sulfuric acid;
    b) holding the catalyst mixture in the catalyst formation reactor at a temperature of about 35 to 45° C. for about 60 to 300 minutes; and
    c) adding the catalyst mixture to the cumene hydroperoxide mixture to form the phenol and acetone mixture,
    wherein the phenol and acetone mixture formed has a reduced level of hydroxyacetone as compared to a phenol and acetone mixture formed using a catalyst that is only sulfuric acid.

16. The method of claim 15, wherein the sulfuric acid is fuming sulfuric acid (oleum).

* * * * *